US006894025B2

(12) United States Patent
Harris

(10) Patent No.: US 6,894,025 B2
(45) Date of Patent: *May 17, 2005

(54) BIOLOGICALLY ACTIVE MOLECULES HAVING THIOL MOIETY CONJUGATED TO POLYMERS CONTAINING ETHYL SULFONE MOIETY

(75) Inventor: J. Milton Harris, Huntsville, AL (US)

(73) Assignee: Nektar Therapeutics AL, Corp., Huntsville, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/647,621

(22) Filed: Aug. 25, 2003

(65) Prior Publication Data

US 2004/0037801 A1 Feb. 26, 2004

Related U.S. Application Data

(60) Continuation of application No. 09/294,188, filed on Apr. 19, 1999, now Pat. No. 6,610,281, which is a division of application No. 09/027,679, filed on Feb. 23, 1998, now Pat. No. 5,900,461, which is a division of application No. 08/473,734, filed on Jun. 7, 1995, now Pat. No. 5,739,208, which is a division of application No. 08/151,481, filed on Nov. 12, 1993, now Pat. No. 5,446,090.

(51) Int. Cl.$^7$ .................. A61K 38/00; A61K 38/54; A01N 37/18; C12N 11/00; C07K 1/00

(52) U.S. Cl. ............... 514/2; 424/94.3; 435/174; 435/188; 530/402; 530/815; 530/816

(58) Field of Search ................. 435/174, 188, 435/68.1; 424/94.3; 514/2; 530/402, 815–16

(56) References Cited

U.S. PATENT DOCUMENTS

| 3,784,524 A | 1/1974 | Morgan |
| 4,002,531 A | 1/1977 | Royer |
| 4,066,581 A | 1/1978 | Sieber |
| 4,066,638 A | 1/1978 | Fuchs et al. |
| 4,101,380 A | 7/1978 | Rubinstein et al. |
| 4,134,887 A | 1/1979 | Fuchs et al. |
| 4,179,337 A | 12/1979 | Davis et al. |
| 4,179,387 A | 12/1979 | Sasazawa et al. |
| 4,228,019 A | 10/1980 | Hunter |
| 4,241,199 A | 12/1980 | Dunleavy |
| 4,280,979 A | 7/1981 | Dunleavy et al. |
| 4,296,097 A | 10/1981 | Lee et al. |
| 4,356,166 A | 10/1982 | Peterson et al. |
| 4,424,311 A | 1/1984 | Nagaoka et al. |
| 4,430,260 A | 2/1984 | Lee et al. |
| 4,473,693 A | 9/1984 | Stewart |
| 4,559,179 A | 12/1985 | Hisamoto et al. |
| 4,616,644 A | 10/1986 | Saferstein et al. |
| 4,670,417 A | 6/1987 | Iwasaki et al. |
| 4,677,027 A | 6/1987 | Porath et al. |
| 4,696,980 A | 9/1987 | Porath |
| 4,766,106 A | 8/1988 | Katre et al. |
| 4,791,192 A | 12/1988 | Nakagawa et al. |
| 4,845,024 A | 7/1989 | Himmelmann et al. |
| 4,871,785 A | 10/1989 | Froix |
| 4,883,864 A | 11/1989 | Scholz |
| 4,902,502 A | 2/1990 | Nitecki et al. |
| 4,917,888 A | 4/1990 | Katre et al. |
| 4,931,544 A | 6/1990 | Katre et al. |
| 4,931,579 A | 6/1990 | Heidenreich et al. |
| 4,965,112 A | 10/1990 | Brinkman et al. |
| 4,973,493 A | 11/1990 | Guire |
| 4,983,494 A | 1/1991 | Kitaguchi et al. |
| 5,080,891 A | 1/1992 | Saifer et al. |
| 5,089,261 A | 2/1992 | Nitecki et al. |
| 5,122,614 A | 6/1992 | Zalipsky |
| 5,153,265 A | 10/1992 | Shadle et al. |
| 5,162,430 A | 11/1992 | Rhee et al. |
| 5,171,264 A | 12/1992 | Merrill |
| 5,414,135 A | 5/1995 | Snow et al. |
| 5,543,332 A | 8/1996 | Lihme et al. |

FOREIGN PATENT DOCUMENTS

| EP | 0 247 860 | 12/1987 |
| EP | 0 622 394 A1 | 11/1994 |
| WO | WO 87/00056 | 1/1987 |
| WO | WO 90/04384 | 5/1990 |
| WO | WO 90/04606 | 5/1990 |
| WO | WO 90/04650 | 5/1990 |
| WO | WO 90/15628 | 12/1990 |
| WO | WO 91/07190 | 5/1991 |
| WO | WO 92/04384 | 3/1992 |
| WO | WO 92/06678 | 4/1992 |
| WO | WO 92/07006 | 4/1992 |
| WO | WO 92/13095 | 8/1992 |
| WO | WO 92/16221 | 10/1992 |
| WO | WO 92/16292 | 10/1992 |
| WO | WO 92/16555 | 10/1992 |
| WO | WO 93/01498 | 1/1993 |

OTHER PUBLICATIONS

Woghiren et al., "Protected Thiol–Polyethylene Glycol: A New Activated Polymer for Reversible Protein Modification," *Bioconjugate Chem.*, 1993, vol. 4, No. 5, pp. 314–318.

Yoshinga et al., "Effects of Coupling Chemistry on the Activity of Poly(Ethylene Glycol)–Modified Alkaline Phosphates," *Journal of Bioactive and Compatible Polymers*, Jan., 1989, vol. 4, pp. 17–24.

CA95:33396, vol. 95 (1981) Minamizono et al., DT3,002, 724.

*Primary Examiner*—David M. Naff
*Assistant Examiner*—Deborah K. Ware
(74) *Attorney, Agent, or Firm*—Alston & Bird LLP

(57) ABSTRACT

A poly(ethylene glycol) derivative is disclosed that is activated with a sulfone moiety for selective attachment to thiol moieties on molecules and surfaces. The activated PEG is water soluble, hydrolytically stable for extended periods, and forms hydrolytically stable linkages with thiol moieties. The linkages generally are not reversible in reducing environments. The PEG derivative is useful for modifying the characteristics of substances including modifying biologically active molecules and surfaces for biocompatibility. Methods for synthesizing the active PEG and for preparing conjugates of the active PEG and other substances, including biologically active substances, are also disclosed.

12 Claims, No Drawings

BIOLOGICALLY ACTIVE MOLECULES HAVING THIOL MOIETY CONJUGATED TO POLYMERS CONTAINING ETHYL SULFONE MOIETY

CROSS REFERENCE TO RELATED APPLICATIONS

This application is a continuation of application Ser. No. 09/294,188, filed Apr. 19, 1999, now U.S. Pat. No. 6,610,281 which is a divisional of application Ser. No. 09/027,679, filed Feb. 23, 1998, now U.S. Pat. No. 5,900,461, which is a divisional of application Ser. No. 08/473,734, filed Jun. 7, 1995, now U.S. Pat. No. 5,739,208, which is a divisional of application Ser. No. 08/151,481, filed Nov. 12, 1993, now U.S. Pat. No. 5,446,090.

FIELD OF THE INVENTION

This invention relates to active derivatives of poly(ethylene glycol) and related hydrophilic polymers and to methods for their synthesis for use in modifying the characteristics of surfaces and molecules.

BACKGROUND OF THE INVENTION

Poly(ethylene glycol) ("PEG") has been studied for use in pharmaceuticals, on artificial implants, and in other applications where biocompatibility is of importance. Various derivatives of poly(ethylene glycol) ("PEG derivatives") have been proposed that have an active moiety for permitting PEG to be attached to pharmaceuticals and implants and to molecules and surfaces generally to modify the physical or chemical characteristics of the molecule or surface.

For example, PEG derivatives have been proposed for coupling PEG to surfaces to control wetting, static buildup, and attachment of other types of molecules to the surface, including proteins or protein residues. More specifically, PEG derivatives have been proposed for attachment to the surfaces of plastic contact lenses to reduce the buildup of proteins and clouding of vision. PEG derivatives have been proposed for attachment to artificial blood vessels to reduce protein buildup and the danger of blockage. PEG derivatives have been proposed for immobilizing proteins on a surface, as in enzymatic catalysis of chemical reactions.

In still further examples, PEG derivatives have been proposed for attachment to molecules, including proteins, for protecting the molecule from chemical attack, to limit adverse side effects of the molecule, or to increase the size of the molecule, thereby potentially to render useful substances that have some medicinal benefit, but are otherwise not useful or are even harmful to a living organism. Small molecules that normally would be excreted through the kidneys are maintained in the blood stream if their size is increased by attaching a biocompatible PEG derivative. Proteins and other substances that create an immune response when injected can be hidden to some degree from the immune system by coupling of a PEG molecule to the protein.

PEG derivatives have also been proposed for affinity partitioning of, for example, enzymes from a cellular mass. In affinity partitioning, the PEG derivative includes a functional group for reversible coupling to an enzyme that is contained within a cellular mass. The PEG and enzyme conjugate is separated from the cellular mass and then the enzyme is separated from the PEG derivative, if desired.

Coupling of PEG derivatives to proteins illustrates some of the problems that have been encountered in attaching PEG to surfaces and molecules. For many surfaces and molecules, the number of sites available for coupling reactions with a PEG derivative is somewhat limited. For example, proteins typically have a limited number and distinct type of reactive sites available for coupling. Even more problematic, some of the reactive sites may be responsible for the protein's biological activity, as when an enzyme catalyzes certain chemical reactions. A PEG derivative that attached to a sufficient number of such sites could adversely affect the activity of the protein.

Reactive sites that form the loci for attachment of PEG derivatives to proteins are dictated by the protein's structure. Proteins, including enzymes, are built of various sequences of alpha-amino acids, which have the general structure $H_2N$—CHR—COOH. The alpha amino moiety ($H_2N$—) of one amino acid joins to the carboxyl moiety (—COOH) of an adjacent amino acid to form amide linkages, which can be represented as —(NH—CHR—CO)$_n$—, where $n$ can be hundreds or thousands. The fragment represented by R can contain reactive sites for protein biological activity and for attachment of PEG derivatives.

For example, in lysine, which is an amino acid forming part of the backbone of most proteins, an —$NH_2$ moiety is present in the epsilon position as well as in the alpha position. The epsilon —$NH_2$ is free for reaction under conditions of basic pH. Much of the art has been directed to developing PEG derivatives for attachment to the epsilon —$NH_2$ moiety of the lysine fraction of a protein. These PEG derivatives all have in common that the lysine amino acid fraction of the protein typically is inactivated, which can be a drawback where lysine is important to protein activity.

Zalipsky U.S. Pat. No. 5,122,614 discloses that PEG molecules activated with an oxycarbonyl-N-dicarboximide functional group can be attached under aqueous, basic conditions by a urethane linkage to the amine group of a polypeptide. Activated PEG-N-succinimide carbonate is said to form stable, hydrolysis-resistant urethane linkages with amine groups. The amine group is shown to be more reactive at basic pHs of from about 8.0 to 9.5, and reactivity falls off sharply at lower pH. However, hydrolysis of the uncoupled PEG derivative also increases sharply at pH's of 8.0 to 9.5. Zalipsky avoids the problem of an increase in the rate of reaction of the uncoupled PEG derivative with water by using an excess of PEG derivative to bind to the protein surface. By using an excess, sufficient reactive epsilon amino sites are bound with PEG to modify the protein before the PEG derivative has an opportunity to become hydrolyzed and unreactive.

Zalipsky's method is adequate for attachment of the lysine fraction of a protein to a PEG derivative at one active site on the PEG derivative. However, if the rate of hydrolysis of the PEG derivative is substantial, then it can be problematic to provide attachment at more than one active site on the PEG molecule, since a simple excess does not slow the rate of hydrolysis.

For example, a linear PEG with active sites at each end will attach to a protein at one end, but, if the rate of hydrolysis is significant, will react with water at the other end to become capped with a relatively nonreactive hydroxyl moiety, represented structurally as —OH, rather than forming a "dumbbell" molecular structure with attached proteins or other desirable groups on each end. A similar problem arises if it is desired to couple a molecule to a surface by a PEG linking agent because the PEG is first attached to the surface or couples to the molecule, and the opposite end of the PEG derivative must remain active for a subsequent reaction. If hydrolysis is a problem, then the opposite end typically becomes inactivated.

Also disclosed in Zalipsky U.S. Pat. No. 5,122,614 are several other PEG derivatives from prior patents. PEG-succinoyl-N-hydroxysuccinimide ester is said to form ester linkages that have limited stability in aqueous media, thus indicating an undesirable short half-life for this derivative. PEG-cyanuric chloride is said to exhibit an undesirable toxicity and to be non-specific for reaction with particular functional groups on a protein. The PEG-cyanuric chloride derivative may therefore have undesirable side effects and may reduce protein activity because it attaches to a number of different types of amino acids at various reactive sites. PEG-phenylcarbonate is said to produce toxic hydrophobic phenol residues that have affinity for proteins. PEG activated with carbonyldiimidazole is said to be too slow in reacting with protein functional groups, requiring long reaction times to obtain sufficient modification of the protein.

Still other PEG derivatives have been proposed for attachment to functional groups on amino acids other than the epsilon $—NH_2$ of lysine. Histidine contains a reactive imino moiety, represented structurally as —N(H)—, but many derivatives that react with epsilon $—NH_2$ also react with —N(H)—. Cysteine contains a reactive thiol moiety, represented structurally as —SH, but the PEG derivative maleimide that is reactive with this moiety is subject to hydrolysis.

As can be seen from the small sampling above, considerable effort has gone into developing various PEG derivatives for attachment to, in particular, the $—NH_2$ moiety on the lysine amino acid fraction of various proteins. Many of these derivatives have proven problematic in their synthesis and use. Some form unstable linkages with the protein that are subject to hydrolysis and therefore do not last very long in aqueous environments, such as in the blood stream. Some form more stable linkages, but are subject to hydrolysis before the linkage is formed, which means that the reactive group on the PEG derivative may be inactivated before the protein can be attached. Some are somewhat toxic and are therefore less suitable for use in vivo. Some are too slow to react to be practically useful. Some result in a loss of protein activity by attaching to sites responsible for the protein's activity. Some are not specific in the sites to which they will attach, which can also result in a loss of desirable activity and in a lack of reproducibility of results.

SUMMARY OF THE INVENTION

The invention provides water soluble and hydrolytically stable derivatives of poly(ethylene glycol) ("PEG") polymers and related hydrophilic polymers having one or more active sulfone moieties. These polymer derivatives with active sulfone moieties are highly selective for coupling with thiol moieties instead of amino moieties on molecules and on surfaces, especially at pHs of about 9 or less. The sulfone moiety, the linkage between the polymer and the sulfone moiety, and the linkage between the thiol moiety and the sulfone moiety are not generally reversible in reducing environments and are stable against hydrolysis for extended periods in aqueous environments at pHs of about 11 or less. Consequently, the physical and chemical characteristics of a wide variety of substances can be modified under demanding aqueous conditions with the active sulfone polymer derivatives. For example, conditions for modification of biologically active substances can be optimized to preserve a high degree of biological activity. Pharmaceuticals from aspirin to penicillin can be usefully modified by attachment of active sulfone polymer derivatives if these pharmaceuticals are modified to contain thiol moieties. Large proteins containing cysteine units, which have active thiol moieties, can also be usefully modified. Techniques of recombinant DNA technology ("genetic engineering") can be used to introduce cysteine groups into desired places in a protein. These cysteines can be coupled to active sulfone polymer derivatives to provide hydrolytically stable linkages on a variety of proteins that do not normally contain cysteine units.

Specific sulfone moieties for the activated polymers of the invention are those having at least two carbon atoms joined to the sulfone group $—SO_2—$ with a reactive site for thiol specific coupling reactions on the second carbon from the sulfone group.

More specifically, the active sulfone moieties comprise vinyl sulfone, the active ethyl sulfones, including the haloethyl sulfones, and the thiol-specific active derivatives of these sulfones. The vinyl sulfone moiety can be represented structurally as $—SO_2—CH=CH_2$; the active ethyl sulfone moiety can be represented structurally as $—SO_2—CH_2—CH_2—Z$ where Z can be halogen or some other leaving group capable of substitution by thiol to form the sulfone and thiol linkage $—SO_2—CH_2—CH_2—S—W$, where W represents a biologically active molecule, a surface, or some other substance. The derivatives of the vinyl and ethyl sulfones can include other substituents, so long as the water solubility and the thiol-specific reactivity of the reactive site on the second carbon are maintained.

The invention includes hydrolytically stable conjugates of substances having thiol moieties with polymer derivatives having active sulfone moieties. For example, a water soluble sulfone-activated PEG polymer can be coupled to a biologically active molecule at a reactive thiol site. The linkage by which the PEG and the biologically active molecule are coupled includes a sulfone moiety coupled to a thiol moiety and has the structure $PEG-SO_2—CH_2—CH_2—S—W$, where W represents the biologically active molecule, whether the sulfone moiety prior to coupling of the PEG was vinyl sulfone or an active ethyl sulfone.

The invention also includes biomaterials comprising a surface having one or more reactive thiol sites and one or more of the water soluble sulfone-activated polymers of the invention coupled to the surface by a sulfone and thiol linkage. Biomaterials and other substances can also be coupled to the sulfone activated polymer derivatives through a linkage other than the sulfone and thiol linkage, such as a conventional amino linkage, to leave a more hydrolytically stable activating group, the sulfone moiety, available for subsequent reactions.

The invention includes a method of synthesizing the activated polymers of the invention. A sulfur containing moiety is bonded directly to a carbon atom of the polymer and then converted to the active sulfone moiety. Alternatively, the sulfone moiety can be prepared by attaching a linking agent that has the sulfone moiety at one terminus to a conventional activated polymer so that the resulting polymer has the sulfone moiety at its terminus.

More specifically, a water soluble polymer having at least one active hydroxyl moiety undergoes a reaction to produce a substituted polymer having a more reactive moiety thereon. The resulting substituted polymer undergoes a reaction to substitute for the more reactive moiety a sulfur-containing moiety having at least two carbon atoms where the sulfur in the sulfur-containing moiety is bonded directly to a carbon atom of the polymer. The sulfur-containing moiety then undergoes reactions to oxidize sulfur, —S—, to sulfone, —$SO_2$—, and to provide a sufficiently reactive site on the second carbon atom of the sulfone containing moiety for formation of linkages with thiol containing moieties.

Still more specifically, the method of synthesizing the activated polymers of the invention comprises reacting poly(ethylene glycol) with a hydroxyl activating compound to form an ester or with a halogen containing derivative to form a halogen substituted PEG. The resulting activated PEG is then reacted with mercaptoethanol to substitute the mercaptoethanol radical for the ester moiety or the halide. The sulfur in the mercaptoethanol moiety is oxidized to sulfone. The ethanol sulfone is activated by either activating the hydroxyl moiety or substituting the hydroxyl moiety with a more active moiety such as halogen. The active ethyl sulfone of PEG can then be converted to vinyl sulfone, if desired, by cleaving the activated hydroxyl or other active moiety and introducing the carbon-carbon double bond adjacent the sulfone group —$SO_2$—.

The invention also includes a method for preparing a conjugate of a substance with a polymer derivative that has an active sulfone moiety. The method includes the step of forming a linkage between the polymer derivative and the substance, which linkage can be between the sulfone moiety and a thiol moiety.

Thus the invention provides activated polymers that are specific in reactivity, stable in water, stable in reducing environments, and that form more stable linkages with surfaces and molecules, including biologically active molecules, than previously has been achieved. The activated polymer can be used to modify the characteristics of surfaces and molecules where biocompatibility is of importance. Because the activated polymer is stable under aqueous conditions and forms stable linkages with thiol moieties, the most favorable reaction conditions can be selected for preserving activity of biologically active substances and for optimizing the rate of reaction for polymer coupling.

DETAILED DESCRIPTION OF THE INVENTION

The synthetic route used to prepare active sulfones of poly(ethylene glycol) and related polymers comprises at least four steps in which sulfur is bound to a polymer molecule and then converted through a series of reactions to an active sulfone functional group. The starting PEG polymer molecule has at least one hydroxyl moiety, —OH, that is available to participate in chemical reactions and is considered to be an "active" hydroxyl moiety. The PEG molecule can have multiple active hydroxyl moieties available for chemical reaction, as is explained below. These active hydroxyl moieties are in fact relatively nonreactive, and the first step in the synthesis is to prepare a PEG having a more reactive moiety.

A more reactive moiety typically will be created by one of two routes, hydroxyl activation or substitution. Other methods are available as should be apparent to the skilled artisan, but hydroxyl activation and substitution are the two most often used. In hydroxyl activation, the hydrogen atom —H on the hydroxyl moiety —OH is replaced with a more active group. Typically, an acid or an acid derivative such as an acid halide is reacted with the PEG to form a reactive ester in which the PEG and the acid moiety are linked through the ester linkage. The acid moiety generally is more reactive than the hydroxyl moiety. Typical esters are the sulfonate, carboxylate, and phosphate esters.

Sulfonyl acid halides that are suitable for use in practicing the invention include methanesulfonyl chloride and p-toluenesulfonyl chloride. Methanesulfonyl chloride is represented structurally as $CH_3SO_2Cl$ and is also known as mesyl chloride. Methanesulfonyl esters are sometimes referred to as mesylates. Para-toluenesulfonyl chloride is represented structurally as $H_3CC_6H_4SO_2Cl$ and is also known as tosyl chloride. Toluenesulfonyl esters are sometimes referred to as tosylates.

In a substitution reaction, the entire —OH group on the PEG is substituted by a more reactive moiety, typically a halide. For example, thionyl chloride, represented structurally as $SOCl_2$, can be reacted with PEG to form a more reactive chlorine substituted PEG. Substitution of the hydroxyl moiety by another moiety is sometimes referred to in the art as hydroxyl activation. The term "hydroxyl activation" should be interpreted herein to mean substitution as well as esterification and other methods of hydroxyl activation.

The terms "group," "functional group," "moiety," "active moiety," "reactive site," and "radical" are somewhat synonymous in the chemical arts and are used in the art and herein to refer to distinct, definable portions or units of a molecule and to units that perform some function or activity and are reactive with other molecules or portions of molecules. In this sense a protein or a protein residue can be considered a molecule or as a functional group or moiety when coupled to a polymer.

The term "PEG" is used in the art and herein to describe any of several condensation polymers of ethylene glycol having the general formula represented by the structure $H(OCH_2CH_2)_nOH$. PEG is also known as polyoxyethylene, polyethylene oxide, polyglycol, and polyether glycol. PEG can be prepared as copolymers of ethylene oxide and many other monomers.

Poly(ethylene glycol) is used in biological applications because it has properties that are highly desirable and is generally approved for biological or biotechnical applications. PEG typically is clear, colorless, odorless, soluble in water, stable to heat, inert to many chemical agents, does not hydrolyze or deteriorate, and is nontoxic. Poly(ethylene glycol) is considered to be biocompatible, which is to say that PEG is capable of coexistence with living tissues or organisms without causing harm. More specifically, PEG is not immunogenic, which is to say that PEG does not tend to produce an immune response in the body. When attached to a moiety having some desirable function in the body, the PEG tends to mask the moiety and can reduce or eliminate any immune response so that an organism can tolerate the presence of the moiety. Accordingly, the sulfone-activated PEGs of the invention should be substantially non-toxic and should not tend substantially to produce an immune response or cause clotting or other undesirable effects.

The second step in the synthesis is to link sulfur directly to a carbon atom in the polymer and in a form that can be converted to an ethyl sulfone or ethyl sulfone derivative having similar reactive properties. "Ethyl" refers to a moiety having an identifiable group of two carbon atoms joined together. The active sulfone PEG derivative requires that the second carbon atom in the chain away from the sulfone group provide a reactive site for linkages of thiol moieties with the sulfone. This result can be achieved by reacting the active moiety produced in the first step mentioned above, which typically will be the ester or halide substituted PEG, in a substitution reaction with an alcohol that also contains a reactive thiol moiety attached to an ethyl group, a thioethanol moiety. The thiol moiety is oxidized to sulfone and the second carbon away from the sulfone on the ethyl group is converted to a reactive site.

Compounds containing thiol moieties, —SH, are organic compounds that resemble alcohols, which contain the hydroxyl moiety —OH, except that in thiols, the oxygen of at least one hydroxyl moiety is replaced by sulfur. The activating moiety on the PEG derivative from the first reaction, which typically is either halide or the acid moiety of an ester, is cleaved from the polymer and is replaced by the alcohol radical of the thioethanol compound. The sulfur in the thiol moiety of the alcohol is linked directly to a carbon on the polymer.

The alcohol should be one that provides a thioethanol moiety for attachment directly to the carbon of the polymer chain, or that can easily be converted to a thioethanol moiety or substituted moiety of similar reactive properties. An example of such an alcohol is mercaptoethanol, which is represented structurally as $HSCH_2CH_2OH$ and is sometimes also called thioethanol.

In the third step of the synthesis, an oxidizing agent is used to convert the sulfur that is attached to the carbon to the sulfone group, —$SO_2$. There are many such oxidizing agents, including hydrogen peroxide and sodium perborate. A catalyst, such as tungstic acid, can be useful. However, the sulfone that is formed is not in a form active for thiol-selective reactions and it is necessary to remove the relatively unreactive hydroxyl moiety of the alcohol that was added in the substitution reaction of the second step.

In the fourth step, the hydroxyl moiety of the alcohol that was added in the second step is converted to a more reactive form, either through activation of the hydroxyl group or through substitution of the hydroxyl group with a more reactive group, similar to the first step in the reaction sequence. Substitution typically is with halide to form a haloethyl sulfone or a derivative thereof having a reactive site on the second carbon removed from the sulfone moiety. Typically, the second carbon on the ethyl group will be activated by a chloride or bromide halogen. Hydroxyl activation should provide a site of similar reactivity, such as the sulfonate ester. Suitable reactants are the acids, acid halides, and others previously mentioned in connection with the first step in the reaction, especially thionyl chloride for substitution of the hydroxyl group with the chlorine atom.

The resulting polymeric activated ethyl sulfone is stable, isolatable, and suitable for thiol-selective coupling reactions. As shown in the examples, PEG chloroethyl sulfone is stable in water at a pH of about 7 or less, but nevertheless can be used to advantage for thiol-selective coupling reactions at conditions of basic pH up to at least about pH 9.

In the thiol coupling reaction, it is possible that the thiol moiety displaces chloride, as in the following reaction:

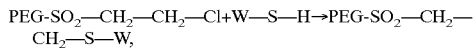

where W represents the moiety to which the thiol moiety SH is linked and can be a biologically active molecule, a surface, or some other substance. However, and while not wishing to be bound by theory, it is believed, based on the observable reaction kinetics as shown in Example 3, that the chloroethyl and other activated ethyl sulfones and reactive derivatives are converted to PEG vinyl sulfone, and that it is the PEG vinyl sulfone or derivative thereof that is actually linked to the thiol moiety. Nevertheless, the resulting sulfone and thiol linkage is not distinguishable, whether from active PEG ethyl sulfone or from PEG vinyl sulfone, and so the active ethyl sulfone can be used at pHs above 7 for linking to thiol groups.

PEG vinyl sulfone is also stable and isolatable and can form thioselective, hydrolytically stable linkages, typically in much less time than the haloethyl sulfone or other activated ethyl sulfone, as explained further below.

In a fifth step that can be added to the synthesis, the activated ethyl sulfone is reacted with any of a variety of bases, such as sodium hydroxide or triethylamine, to form PEG vinyl sulfone or one of its active derivatives for use in thiolselective coupling reactions.

As shown in the examples below, especially Example 3, PEG vinyl sulfone reacts quickly with thiol moieties and is stable against hydrolysis in water of pH less than about 11 for at least several days. The reaction can be represented as follows:

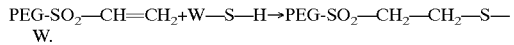

The thiol moiety is said to add "across the double bond." The W-S moiety adds to the terminal $CH_2$ of the double bond, which is the second carbon from the sulfone group $SO_2$. The hydrogen H adds to the CH of the double bond. However, at a pH of above about 9, selectivity of the sulfone moiety for thiol is diminished and the sulfone moiety becomes somewhat more reactive with amino groups.

Alternatively to the above synthesis, the sulfone-activated PEG derivatives can be prepared by attaching a linking agent having a sulfone moiety to a PEG activated with a different functional group. For example, an amino activated PEG, PEG-$NH_2$, is reacted under favorable conditions of pH of about 9 or less with a small molecule that has a succinimidyl active ester moiety NHS—$O_2$C— at one terminus and a sulfone moiety, vinyl sulfone —$SO_2$—CH=$CH_2$, at the other terminus. The amino activated PEG forms a stable linkage with the succinimidyl ester. The resulting PEG is activated with the vinyl sulfone moiety at the terminus and is hydrolytically stable. The reaction and the resulting vinyl sulfone activated PEG are represented structurally as follows:

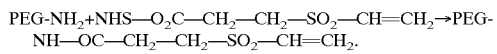

A similar activated PEG could be achieved by reacting an amine-activated PEG such as succinimidyl active ester PEG, PEG-$CO_2$—NHS, with a small molecule that has an amine moiety at one terminus and a vinyl sulfone moiety at the other terminus. The succinimidyl ester forms a stable linkage with the amine moiety as follows:

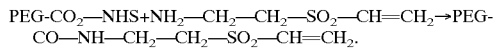

The active PEG sulfones of the invention can be of any molecular weight and can be linear or branched with hundreds of arms. The PEG can be substituted or unsubstituted so long as at least one reactive site is available for substitution with the sulfone moieties. PEG typically has average molecular weights of from 200 to 100,000 and its biological properties can vary with molecular weight and depending on the degree of branching and substitution, so not all of these derivatives may be useful for biological or biotechnical applications. For most biological and biotechnical applications, substantially linear, straight-chain PEG vinyl sulfone or bis vinyl sulfone or activated ethyl sulfone will be used, substantially unsubstituted except for the vinyl sulfone or ethyl sulfone moieties and, where desired, other additional functional groups. For many biological and biotechnical applications, the substituents would typically be unreactive groups such as hydrogen H—and methyl $CH_3$—("m-PEG").

The PEG can have more than one vinyl sulfone or precursor moiety attached or the PEG can be capped on one end with a relatively nonreactive moiety such as the methyl radical, —CH$_3$. The capped form can be useful, for example, if it is desirable simply to attach the polymer chains at various thiol sites along a protein chain. Attachment of PEG molecules to a biologically active molecule such as a protein or other pharmaceutical or to a surface is sometimes referred to as "PEGylation."

A linear PEG with active hydroxyls at each end can be activated at each end with vinyl sulfone or its precursor or derivatives of similar reactivity to become bifunctional. The bifunctional structure, PEG bis vinyl sulfone, for example, is sometimes referred to as a dumbbell structure and can be used, for example, as a linker or spacer to attach a biologically active molecule to a surface or to attach more than one such biologically active molecule to the PEG molecule. The stability of the sulfone moiety against hydrolysis makes it particularly useful for bifunctional or heterobifunctional applications.

Another application for PEG vinyl sulfone and its precursor is dendritic activated PEG in which multiple arms of PEG are attached to a central core structure. Dendritic PEG structures can be highly branched and are commonly known as "star" molecules. Star molecules are generally described in Merrill U.S. Pat. No. 5,171,264, the contents of which are incorporated herein by reference. The sulfone moieties can be used to provide an active, functional group on the end of the PEG chain extending from the core and as a linker for joining a functional group to the star molecule arms.

PEG vinyl sulfone and its precursors and derivatives can be used for attachment directly to surfaces and molecules having a thiol moiety. However, more typically a heterobifunctional PEG derivative having a sulfone moiety on one terminus and a different functional moiety on the opposite terminus group will be attached by the different moiety to a surface or molecule. When substituted with one of the other active moieties, the heterobifunctional PEG dumbbell structure can be used, for example, to carry a protein or other biologically active molecule by sulfone linkages on one end and by another linkage on the other end, such as an amine linkage, to produce a molecule having two different activities. A heterobifunctional PEG having a sulfone moiety on one end and an amine specific moiety on the other end could be attached to both cysteine and lysine fractions of proteins. A stable amine linkage can be achieved and then the hydrolytically stable unreacted sulfone moiety is available for subsequent thiol-specific reactions as desired.

Other active groups for heterobifunctional sulfone-activated PEGs can be selected from among a wide variety of compounds. For biological and biotechnical applications, the substituents would typically be selected from reactive moieties typically used in PEG chemistry to activate PEG such as the aldehydes, trifluoroethylsulfonate, which is also sometimes called tresylate, n-hydroxylsuccinimide ester, cyanuric chloride, cyanuric fluoride, acyl azide, succinate, the p-diazo benzyl group, the 3-(p-diazophenyloxy)-2-hydroxy propyloxy group, and others.

Examples of active moieties other than sulfone are shown in Davis et al. U.S. Pat. No. 4,179,337; Lee et al. U.S. Pat. Nos. 4,296,097 and 4,430,260; Iwasaki et al. U.S. Pat. No. 4,670,417; Katre et al. U.S. Pat. Nos. 4,766,106; 4,917,888; and 4,931,544; Nakagawa et al. U.S. Pat. No. 4,791,192; Nitecki et al. U.S. Pat. Nos. 4,902,502 and 5,089,261; Saifer U.S. Pat. No. 5,080,891; Zalipsky U.S. Pat. No. 5,122,614; Shadle et al. U.S. Pat. No. 5,153,265; Rhee et al. U.S. Pat. No. 5,162,430; European Patent Application Publication No. 0 247 860; and PCT International Application Nos. US86/01252; GB89/01261; GB89/01262; GB89/01263; US90/03252; US90/06843; US91/06103; US92/00432; and US92/02047, the contents of which are incorporated herein by reference.

It should be apparent to the skilled artisan that the dumbbell structures discussed above could be used to carry a wide variety of substituents and combinations of substituents. Pharmaceuticals such as aspirin, vitamins, penicillin, and others too numerous to mention; polypeptides or proteins and protein fragments of various functionalities and molecular weights; cells of various types; surfaces for biomaterials, almost any substance could be modified. As used herein, the term "protein" should be understood to include peptides and polypeptides, which are polymers of amino acids. The term "biomaterial" means a material, typically synthetic and sometimes made of plastic, that is suitable for implanting in a living body to repair damaged or diseased parts. An example of a biomaterial is artificial blood vessels.

One straight chain PEG derivative of the invention for biological and biotechnical applications has the basic structure R—(OCH$_2$CH$_2$)$_n$—Y. The PEG monomer OCH$_2$CH$_2$ preferably is substantially unsubstituted and unbranched along the polymer backbone. The subscript "$n$" can equal from about 5 to 3,000. A more typical range is from about 5 to 2,200, which corresponds to a molecular weight of from about 220 to 100,000. Still more typical is a range of from about 34 to 1,100, which corresponds to a molecular weight range of from about 1,500 to 50,000. Most applications will be accomplished with molecular weights in the neighborhood of 2,000 to 5,000, which corresponds to a value of $n$ of from about 45 to 110.

In the above structure, Y represents —SO$_2$—CH=CH$_2$ or —SO$_2$—CH$_2$—CH$_2$—X where X is a halogen. R represents a group that may be the same or different from Y. R can be H—, H$_3$C—, CH$_2$=CH—SO$_2$—, Cl—CH$_2$—CH$_2$—SO$_2$—, or a polymer activating group other than CH$_2$=CH—SO$_2$—, Cl—CH$_2$—CH$_2$—SO$_2$—, such as is referred to with respect to the above patents and published patent applications.

The active polymer derivatives are water soluble and hydrolytically stable and produce water soluble and hydrolytically stable linkages with thiol groups. The derivatives are considered infinitely soluble in water or as approaching infinite solubility and can enable otherwise insoluble molecules to pass into solution when conjugated with the derivative.

Hydrolytic stability of the derivatives means that the linkage between the polymer and the sulfone moiety is stable in water and that the vinyl sulfone moiety does not react with water at a pH of less than about 11 for an extended period of time of at least several days, and potentially indefinitely, as shown in Example 3 below. The activated ethyl sulfone can be converted to the vinyl sulfone at conditions of basic pH, with the same resulting stability. Hydrolytic stability of the thiol linkage means that conjugates of the activated polymer and a substance having a thiol moiety are stable at the sulfone-thiol linkage for an extended period of time in aqueous environments at a pH of below about 11. Most proteins could be expected to lose their activity at a caustic pH of 11 or higher, so it should be apparent to the skilled artisan that many applications for the active sulfone PEG derivatives will be at pHs of less than 11, regardless of the stability of the sulfone moiety at higher pH.

To be useful for modification of proteins and other substances, it is only necessary that the sulfone be stable for a period of time sufficient to permit the sulfone to react with a reactive thiol moiety on the protein or other substance. The rate of reaction of the sulfone moiety with thiol can vary with pH, as shown in Example 2 below, from about 2 minutes to 30 minutes, which is much faster than the rate of hydrolysis, if any. Vinyl sulfone could be expected to react with thiol over a much broader range of reaction times since it is stable for long periods of time. Also, as shown in Example 3 below, at conditions of basic pH chloroethyl sulfone is not hydrolyzed, but is converted to vinyl sulfone, which remains stable for several days and is even more reactive toward thiol groups. Accordingly, for the purpose of modifying the characteristics of substances, the active ethyl sulfones can also be considered to be hydrolytically stable for an extended period of time over a broad pH range.

Other water soluble polymers than PEG are believed to be suitable for similar modification and activation with an active sulfone moiety. These other polymers include poly (vinyl alcohol) ("PVA"); other poly(alkylene oxides) such as poly(propylene glycol) ("PPG") and the like; and poly (oxyethylated polyols) such as poly(oxyethylated glycerol), poly(oxyethylated sorbitol), and poly(oxyethylated glucose), and the like. The polymers can be homopolymers or random or block copolymers and terpolymers based on the monomers of the above polymers, straight chain or branched, or substituted or unsubstituted similar to PEG, but having at least one active site available for reaction to form the sulfone moiety.

The following Example 1 shows the synthesis, isolation, and characterization of poly(ethylene glycol) chloroethyl sulfone followed by the preparation of poly(ethylene glycol) vinyl sulfone from the chloroethyl sulfone. Preparation of other polymeric sulfones having a reactive site on the second carbon from the sulfone group is similar and the steps for doing so should be apparent to the skilled artisan based on Example 1 below and the polymers listed above.

EXAMPLE 1

Synthesis

The reaction steps can be illustrated structurally as follows:

  (1)

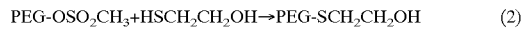  (2)

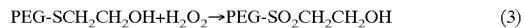  (3)

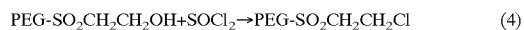  (4)

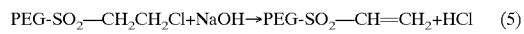  (5)

Each of the above reactions is described in detail below:

Reaction 1. Reaction 1 represents the preparation of the methane sulfonyl ester of poly(ethylene glycol), which can also be referred to as the methanesulfonate or mesylate of poly(ethylene glycol). The tosylate and the halides can be prepared by similar procedures, which are believed to be apparent to the skilled artisan.

To prepare the mesylate, twenty-five grams of PEG of molecular weight 3400 was dried by azeotropic distillation in 150 ml of toluene. Approximately half of the toluene was distilled off in drying the PEG. Forty ml of dry dichloromethane was added to the toluene and PEG solution, followed by cooling in an ice bath. To the cooled solution was added 1.230 ml of distilled methanesulfonyl chloride, which is an equivalent weight of 1.06 with respect to PEG hydroxyl groups, and 2.664 ml of dry triethylamine, which is an equivalent weight of 1.3 with respect to PEG hydroxyl groups. "Equivalent weight" as used above can be thought of as "combining weight" and refers to the weight of a compound that will react with an equivalent weight of PEG hydroxyl groups.

The reaction was permitted to sit overnight during which time it warmed to room temperature. Triethylammonium hydrochloride precipitated and the precipitate was removed by filtration. Thereafter, the volume was reduced by rotary evaporation to 20 ml. The mesylate was precipitated by addition to 100 ml of cold dry ethyl ether. Nuclear magnetic resonance (NMR) analysis showed 100% conversion of hydroxyl groups to mesylate groups.

Reaction 2. Reaction 2 represents the formation of poly (ethylene glycol) mercaptoethanol by reaction of the mesylate with mercaptoethanol. The reaction causes the methanesulfonate radical to be displaced from the PEG. The sulfur in the mercaptoethanol radical is attached directly to the carbon in the carbon-carbon backbone of the PEG.

Twenty grams of the mesylate from reaction 1 was dissolved in 150 ml of distilled water. The solution of mesylate and water was cooled by immersion in an ice bath. To the cooled solution was added 2.366 ml of mercaptoethanol, which is 3 equivalent weights with respect to PEG hydroxyl groups. Also added was 16.86 ml of 2N NaOH base. The reaction was refluxed for 3 hours, which means that the vapors rising from the reaction were continuously condensed and allowed to flow back into the reaction.

The poly(ethylene glycol) mercaptoethanol product was extracted three times with dichloromethane using approximately 25 ml of dichloromethane each time. The organic fractions were collected and dried over anhydrous magnesium sulfate. The volume was reduced to 20 ml and the product was precipitated by addition to 150 ml of cold dry ether.

NMR analysis in $d_6$-DMSO dimethyl sulfoxide gave the following peaks for PEG-SCH$_2$CH$_2$OH: 2.57 ppm, triplet, —CH$_2$—S—; 2.65 ppm, triplet, —S—CH$_2$—; 3.5 ppm, backbone singlet; and 4.76 ppm, triplet, —OH. The hydroxyl peak at 4.76 ppm indicated 81% substitution. However, the 2.65 ppm peak for —S—CH$_2$— indicated 100% substitution. It has been observed that hydroxyl peaks frequently give low figures on percent substitution, and so the 2.65 ppm peak for —S—CH$_2$— is considered to be more reliable and to confirm 100% substitution.

Reaction 3. Reaction 3 represents peroxide oxidation of the poly(ethylene glycol) mercaptoethanol product to convert the sulfur, S, to sulfone, SO$_2$. PEG ethanol sulfone is produced.

Twenty grams of PEG-SCH$_2$CH$_2$OH was dissolved in 30 ml of 0.123M tungstic acid solution and cooled in an ice bath. The tungstic acid solution was prepared by dissolving the acid in sodium hydroxide solution of pH 11.5 and then adjusting the pH to 5.6 with glacial acetic acid. Twenty ml of distilled water and 2.876 ml of 30% hydrogen peroxide, which has an equivalent weight of 2.5 with respect to hydroxyl groups, was added to the solution of tungstic acid and poly(ethylene glycol) mercaptoethanol and the reaction was permitted to warm overnight to room temperature.

The oxidized product was extracted three times with dichloromethane using 25 ml of dichloromethane each time. The collected organic fractions were washed with dilute aqueous sodium bicarbonate and dried with anhydrous magnesium sulfate. The volume was reduced to 20 ml. The PEG ethanol sulfone product was precipitated by addition to cold dry ethyl ether.

NMR analysis in $d_6$-DMSO dimethyl sulfoxide gave the following peaks for PEG-SO$_2$CH$_2$CH$_2$OH: 3.25 ppm, triplet, —CH$_2$—SO$_2$—; 3.37 ppm, triplet, —SO$_2$—CH$_2$—; 3.50 ppm, backbone; 3.77 ppm, triplet, —CH$_2$OH; 5.04 ppm, triplet, —OH. The hydroxyl peak at 5.04 ppm indicated 85% substitution. However, the peak at 3.37 ppm for —SO$_2$—CH$_2$— indicated 100% substitution and is considered to be more reliable.

Reaction 4. Reaction 4 represents the final step in synthesis, isolation, and characterization of poly(ethylene glycol) chloroethyl sulfone.

To synthesize the product, twenty grams of PEG-SO$_2$CH$_2$CH$_2$OH poly(ethylene glycol) ethanol sulfone was dissolved in 100 ml of freshly distilled thionyl chloride and the solution was refluxed overnight. The thionyl chloride had been distilled over quinoline. Excess thionyl chloride was removed by distillation. Fifty milliliters of toluene and 50 ml of dichloromethane were added and removed by distillation.

To isolate the product, the PEG chloroethyl sulfone was dissolved in 20 ml of dichloromethane and precipitated by addition to 100 ml of cold dry ethyl ether. The precipitate was recrystallized from 50 ml of ethyl acetate to isolate the product.

Nuclear magnetic resonance was used to characterize the product. NMR analysis of PEG-SO$_2$CH$_2$CH$_2$Cl in $d_6$-DMSO dimethyl sulfoxide gave the following peaks: 3.50 ppm, backbone; 3.64 ppm, triplet, —CH$_2$SO$_2$—; 3.80 ppm, triplet, —SO$_2$—CH$_2$—. A small hydroxyl impurity triplet appeared at 3.94 ppm. Calculation of the percentage substitution was difficult for this spectrum because of the proximity of the important peaks to the very large backbone peak.

Reaction 5. Reaction 5 represents conversion of poly(ethylene glycol) chloroethyl sulfone from reaction step 4 to poly(ethylene glycol) vinyl sulfone and isolation and characterization of the vinyl sulfone product.

The PEG vinyl sulfone was readily prepared by dissolving solid PEG chloroethyl sulfone in dichloromethane solvent followed by addition of two equivalents of NaOH base. The solution was filtered to remove the base and the solvent was evaporated to isolate the final product PEG-SO$_2$—CH=CH$_2$ PEG vinyl sulfone.

The PEG vinyl sulfone was characterized by NMR analysis in $d_6$-DMSO dimethyl sulfoxide. NMR analysis showed the following peaks: 3.50 ppm, backbone; 3.73 ppm, triplet, —CH$_2$—SO$_2$—; 6.21 ppm, triplet, =CH$_2$; 6.97 ppm, doublet of doublets, —SO$_2$—CH—. The 6.97 ppm peak for —SO$_2$—CH— indicated 84% substitution. The 6.21 ppm peak for =CH$_2$ indicated 94% substitution. Titration with mercaptoethanol and 2,2'-dithiodipyridine indicated 95% substitution.

EXAMPLE 2

Thiol-selective Reactivity

Example 2 shows that PEG vinyl sulfone and its precursor PEG chloroethyl sulfone are significantly more reactive with thiol groups (—SH) than with amino groups (—NH$_2$) or imino groups (—NH—). Compounds containing thiol groups are organic compounds that resemble alcohols, which contain the hydroxyl group —OH, except that in thiols, the oxygen of the hydroxyl group is replaced by sulfur. Thiols sometimes are also called sulfhydryls or mercaptans. PEG vinyl sulfone contains the vinyl sulfone group —SO$_2$—CH=CH$_2$. PEG chloroethyl sulfone contains the chloroethyl sulfone group —SO$_2$CH$_2$CH$_2$Cl.

Selectivity for thiols is important in protein modification because it means that cysteine units (containing —SH) will be modified in preference to lysine units (containing —NH$_2$) and histidine units (containing —NH—). The selectivity of PEG vinyl sulfone for thiols means that PEG can be selectively attached to cysteine units, thus preserving protein activity for specific proteins and controlling the number of PEG molecules attached to the protein.

The relative reactivity of PEG vinyl sulfone with thiol and amino groups was determined by measuring the rates of reaction of PEG vinyl sulfone with N-α-acetyl lysine methyl ester and with mercaptoethanol. N-α-acetyl lysine methyl ester is a lysine model containing an amino group and is abbreviated Lys-NH$_2$. Mercaptoethanol serves as a cysteine model containing a thiol group and is abbreviated Cys-SH. Relative reactivity of PEG chloroethyl sulfone was similarly determined. This molecule may serve as a "protected" form of the vinyl sulfone since it is stable in acid but converts to PEG vinyl sulfone upon addition of base.

Reactivity for PEG vinyl sulfone and for the PEG chloroethyl sulfone precursor was investigated at pH 8.0, pH 9.0, and at pH 9.5. Buffers for controlling the pH were 0.1 M phosphate at pH 8.0 and 0.1 M borate at pH 9.0 and at pH 9.5. For measurement of mercaptoethanol reactivity, 5 mM ethylenediamine tetraacetic acid (EDTA) was added to both buffers to retard conversion of thiol to disulfide.

For reaction of the PEG derivatives of the invention with Lys-NH$_2$, a 3 mM solution of the PEG derivative was added under stirring to a 0.3 mM Lys-NH$_2$ solution in the appropriate buffer for each of the three levels of basic pH. The reaction was monitored by addition of fluorescamine to the reaction solution to produce a fluorescent derivative from reaction with remaining amino groups. The monitoring step was performed by adding 50 μL of reaction mixture to 1.950 mL of phosphate buffer of ph 8.0 followed by adding 1.0 mL of fluorescamine solution under vigorous stirring. The fluorescamine solution was 0.3 mg fluorescamine per ml of acetone.

Fluorescence was measured 10 minutes after mixing. Excitation was shown at wavelength 390 nm. Light emission occurred at 475 nm. No reaction was observed in 24 hours for either PEG vinyl sulfone or PEG chloroethyl sulfone at pH 8.0. At pH 9.5 the reaction was slow, but all amino groups were reacted after several days.

For reaction of the PEG vinyl sulfone and PEG chloroethyl sulfone precursor with Cys-SH, a 2 mM solution of the PEG derivative was added to a 0.2 mM solution of Cys-SH in the appropriate buffer for each of the three levels of basic pH. The reaction was monitored by adding 4-dithiopyridine to the reaction solution. The 4-dithiopyridine compound reacts with Cys-SH to produce 4-thiopyridone, which absorbs ultraviolet light.

The monitoring step was performed by adding 50 μL of reaction mixture to 0.950 mL of 0.1 M phosphate buffer at pH 8.0 and containing 5 mM EDTA, followed by adding one mL of 2 mM 4-dithiopyridine in the same buffer.

Absorbance of 4-thiopyridone was measured at 324 nm. Both PEG vinyl sulfone and PEG chloroethyl sulfone showed reactivity toward Cys-SH, with PEG vinyl sulfone showing greater reactivity. At pH 9.0 the reaction is over within two minutes using the vinyl sulfone and within 15 minutes using the chloroethyl sulfone. However, these reactions were too fast for determination of accurate rate constants. At pH 8.0 the reactions were slower, but still complete in one hour for vinyl sulfone and in three hours for the chloroethyl sulfone. The conversion of chloroethyl sulfone to vinyl sulfone is significantly slower than the reaction of vinyl sulfone with Cys-SH. Thus the rate of reaction for chloroethyl sulfone with Cys-SH appears to be dependent on the rate of conversion of chloroethyl sulfone to vinyl sulfone. Nevertheless, these reaction rates were still much faster than for the reaction with Lys-NH2.

The above kinetic studies demonstrate the following points. PEG vinyl sulfone is much more reactive with thiol groups than with amino groups, indicating that attachment of PEG vinyl sulfone to a protein containing both cysteine and lysine groups proceeds primarily by reaction with cysteine. Since reactivity with amino groups is similar to imino groups, then reactivity of histidine subunits will also be much lower than reactivity with cysteine subunits. Also, selectivity toward thiol groups is accentuated at lower pH values for PEG chloroethyl sulfone and PEG vinyl sulfone, although the reactions of PEG chloroethyl sulfone are somewhat slower.

The utility of many PEG derivatives is limited because they react rapidly with water, thus interfering with attempts to attach the derivative to molecules and surfaces under aqueous conditions. The following Example 3 shows that PEG vinyl sulfone and PEG chloroethyl sulfone are stable in water.

EXAMPLE 3

Hydrolytic Stability

PEG vinyl sulfone was dissolved in heavy water, $D_2O$ deuterium oxide, and monitored by NMR. Reaction did not occur. A solution of PEG chloroethyl sulfone produced PEG vinyl sulfone in heavy water that was buffered with borate to pH 9.0. Monitoring with NMR showed that PEG vinyl sulfone, once produced, was stable for three days in heavy water.

PEG chloroethyl sulfone is stable in water until solution becomes basic, at which time it is converted into vinyl sulfone. Conversion to vinyl sulfone has been demonstrated by dissolving PEG chloroethyl sulfone in water at pH 7 and in borate buffer at pH 9. The PEG derivative is extracted into methylene chloride. Removal of methylene chloride, followed by NMR analysis showed that PEG chloroethyl sulfone is stable at a neutral pH of 7.0, and reacts with base to produce PEG vinyl sulfone.

Vinyl sulfone is stable for several days in water, even at basic pH. Extensive hydrolytic stability and thiol-specific reactivity of PEG vinyl sulfone means that PEG vinyl sulfone and its precursor are useful for modification of molecules and surfaces under aqueous conditions, as shown in the following Example 4.

EXAMPLE 4

Protein Conjugation

Protein modification was demonstrated by attachment of the PEG derivative to bovine serum albumin (BSA) by two different methods. BSA is a protein. Native unmodified BSA contains cystine groups which do not contain thiol groups. The cystine units are tied up as disulfide linkages, S—S.

In the first method, m-PEG vinyl sulfone of molecular weight 5,000 was reacted with unmodified BSA for 24 hours in a 0.1 M borate buffer at pH 9.5 at room temperature. The solution contained 1 mg of BSA and 1 mg of m-PEG vinyl sulfone of molecular weight 5,000 per ml of solution. The results from the Example 2 model compounds had indicated that lysine subunits (and possibly histidine subunits) would be modified under these relatively basic conditions and in the absence of free thiol groups available for reaction.

Attachment to lysine subunits was demonstrated in two ways. First, size exclusion chromatography showed that the molecular weight of the protein had increased by approximately 50%, thus indicating attachment of approximately 10 PEGs to the protein. Second, fluorescamine analysis showed that the number of lysine groups in the BSA molecule had been reduced by approximately ten.

In the second method, the BSA was treated with tributylphosphine to reduce the disulfide S—S bonds to thiol groups, —SH, which are available for reaction. The modified BSA was then treated with PEG chloroethyl sulfone at pH 8.0 in a 0.1 M phosphate buffer at room temperature for 1 hour. The solution contained 1 mg of modified BSA and 1 mg of m-PEG chloroethyl sulfone of molecular weight 5,000 per ml of solution. The results showed that lysine groups were unreactive under these conditions. However, thiol groups were reactive.

Attachment of the PEG to the protein was demonstrated by size exclusion chromatography, which showed an increase in the molecular weight of the protein by about 25%. Fluorescamine analysis indicated no change in number of lysine subunits in the protein, thus confirming that PEG attachment did not take place on lysine subunits. Substitution on thiol groups was thereby confirmed.

The invention claimed herein has been described with respect to particular exemplified embodiments. However, the foregoing description is not intended to limit the invention to the exemplified embodiments, and the skilled artisan should recognize that variations can be made within the spirit and scope of the invention as described in the foregoing specification. On the contrary, the invention includes all alternatives, modifications, and equivalents that may be included within the true spirit and scope of the invention as defined by the appended claims.

What is claimed is:

1. A hydrolytically stable, biologically active conjugate that is the reaction product of a biologically active molecule having a reactive thiol moiety and a water-soluble polymer having an active ethyl sulfone moiety having a reactive site located at the second carbon from the sulfone group and wherein said sulfone moiety forms a linkage with said reactive thiol moiety of said biologically active molecule to form said conjugate.

2. The conjugate of claim 1 wherein said biologically active molecule is a protein and said reactive thiol moiety is contained within a cysteine moiety of said protein.

3. The conjugate of claim 1 wherein said water soluble polymer is selected from the group consisting of poly (alkylene oxides), poly(oxyethylated polyols), and poly (olefinic alcohols).

4. The conjugate of claim 1 wherein said water soluble polymer includes a second active moiety, which may be the same or different from said active sulfone moiety, and wherein said second active moiety forms a linkage with a second biologically active molecule.

5. The conjugate of claim 1 wherein said biologically active moiety is selected from the group consisting of proteins, pharmaceuticals, cells, vitamins, and combinations thereof.

6. The conjugate of claim 1 wherein said ethyl sulfone moiety is a haloethyl sulfone.

7. The conjugate of claim 1 wherein said water soluble polymer is poly(ethylene glycol).

8. A biologically active conjugate that is the reaction product of an activated water soluble polymer having at least one active ethyl sulfone moiety that is selective for reaction with thiol moieties and at least one other moiety that is selective for reaction with amino moieties; a first protein having a thiol moiety wherein said thiol moiety forms a hydrolytically stable linkage with said ethyl sulfone moiety on said polymer; and a second protein having an amino moiety wherein said amino moiety forms a linkage with paid other moiety on said polymer.

9. The conjugate of claim 8 wherein said first protein contains cysteine units and said second protein contains lysine units.

10. The conjugate of claim 8 wherein said water soluble polymer is selected from the group consisting of poly (alkylene oxides), poly(oxyethylated polyols), and poly (olefinic alcohols).

11. The conjugate of claim 8 wherein said conjugate is a dumbbell structure.

12. A hydrolytically stable biologically active conjugate that is the reaction product of biologically active molecules, each having a reactive thiol moiety, and a water soluble polymer having at least two active ethyl sulfone moieties, each active ethyl sulfone moiety having a reactive site located at the second carbon from the sulfone group and wherein said sulfone moieties form a linkage with said reactive thiol moieties of said biologically active molecules to form said conjugate.

* * * * *

UNITED STATES PATENT AND TRADEMARK OFFICE
CERTIFICATE OF CORRECTION

PATENT NO. : 6,894,025 B2
DATED : May 17, 2005
INVENTOR(S) : Harris

It is certified that error appears in the above-identified patent and that said Letters Patent is hereby corrected as shown below:

Column 17,
Line 7, "paid" should read -- said --.

Signed and Sealed this

Twelfth Day of July, 2005

JON W. DUDAS
*Director of the United States Patent and Trademark Office*